United States Patent [19]

Laurent et al.

[11] 3,956,347

[45] May 11, 1976

[54] NOVEL PREGNANOIC ACID DERIVATIVES

[75] Inventors: Henry Laurent; Rudolf Wiechert; Klaus Mengel; Hans Wendt, all of Berlin, Germany

[73] Assignee: Schering Aktiengesellschaft, Berlin & Bergkamen, Germany

[22] Filed: Apr. 15, 1974

[21] Appl. No.: 460,905

[30] Foreign Application Priority Data
Apr. 14, 1973  Germany............................ 2319479
Apr. 14, 1973  Germany............................ 2319478
Apr. 14, 1973  Germany............................ 2319477

[52] U.S. Cl............................ 260/397.1; 260/397.45; 424/238
[51] Int. Cl.² ............................................ C07J 3/00
[58] Field of Search .................................. 260/397.1

[56] References Cited
UNITED STATES PATENTS

| | | |
|---|---|---|
| 3,247,189 | 4/1966 | Wettstein et al............ 260/239.55 |
| 3,463,798 | 8/1969 | Godtfredsen et al. ........ 260/397.45 |
| 3,766,213 | 10/1973 | Furst et al...................... 260/343.2 |
| 3,824,260 | 7/1974 | Laurent et al................. 260/397.1 |
| 3,906,095 | 9/1975 | Laurent et al................. 260/397.1 |

Primary Examiner—Elbert L. Roberts
Attorney, Agent, or Firm—Millen, Raptes & White

[57] ABSTRACT

Steroids of the formula

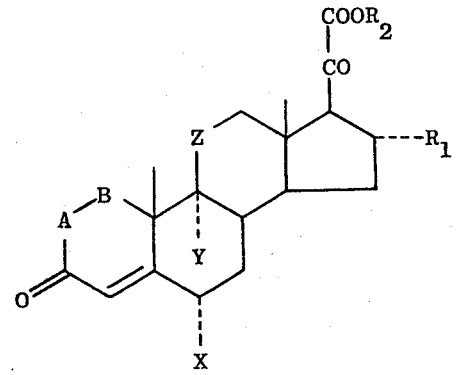

wherein X is a hydrogen atom, a halogen atom or methyl; Y is a hydrogen atom or a halogen atom; Z is carbonyl, β-acyloxymethylene or, when Y is a hydrogen atom, also methylene; $R_1$ is a hydrogen atom or methyl; $R_2$ is a hydrogen atom, an alkali metal atom or optionally substituted hydrocarbon; and —A—B— is —CH=CH—, —CCl=CH— or when at least one of X, Y and $R_1$ is other than a hydrogen atom, —CH$_2$—CH$_2$—, which can be produced by oxidizing a corresponding 20-hydroxy steroid or a corresponding 21-aldehyde, possess topical anti-inflammatory activity.

37 Claims, No Drawings

NOVEL PREGNANOIC ACID DERIVATIVES

BACKGROUND OF THE INVENTION

This invention relates to novel pregnanoic acid derivatives. One of us, with others, has published the isolation of 6α-fluoro-11β-hydroxy-3,20-dioxo-16α-methyl-1,4-pregnadien-21-oic acid (Compound I) as a water-soluble metabolite of fluocortolone in humans. E. Gerhards et al., Acta Endocrinologica, 68 (1971) 98–126. The preparation of the ethyl ester thereof for characterization purposes was also reported in that publication.

We have found that structurally related compounds as defined hereinafter possess valuable pharmacological activity and that they can be prepared synthetically by the methods described hereinafter.

Compounds otherwise corresponding to those of Formula I below but wherein Z is a halogen methylene or hydroxymethylene are the subject matter of Application Ser. No. 284,710, filed Aug. 30, 1972.

SUMMARY OF THE INVENTION

In one aspect, this invention relates to novel compounds of the general Formula I

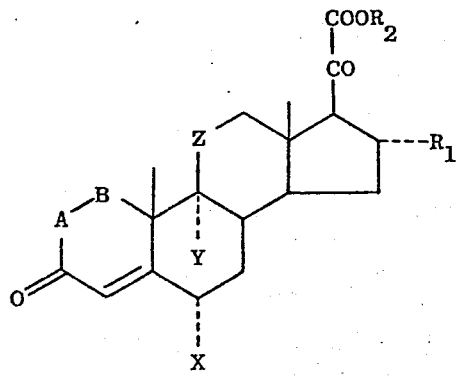

I wherein X is a hydrogen atom, a halogen atom or methyl; Y is a hydrogen atom or a halogen atom; Z is carbonyl, β-acyloxymethylene or, when Y is a hydrogen atom, also methylene; $R_1$ is a hydrogen atom or methyl; $R_2$ is a hydrogen atom, an alkali metal atom or optionally substituted hydrocarbon; and —A—B— is —CH=CH—, —CCl=CH— or when at least one of X, Y and $R_1$ is other than a hydrogen atom, —CH$_2$—CH$_2$—.

In a process aspect, this invention relates to a process for the preparation of the pregnanoic acid derivatives of general Formula I wherein a. the 20-hydroxy group of a compound of general Formula II

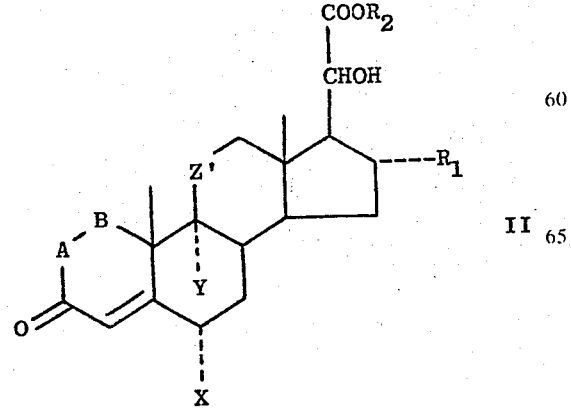

II wherein —A—B—, X, Y, $R_1$ and $R_2$ have the values given in Formula I and Z' is Z or hydroxymethylene, is oxidized in a conventional manner, any free hydroxy group in the 11-position being oxidized or esterified and, optionally thereafter a thus-produced 21-ester of general Formula I are saponified or transesterified or a thus-produced free acid of general Formula I is converted into a salt thereof or is esterified; or b. a steroid aldehyde of general Formula III

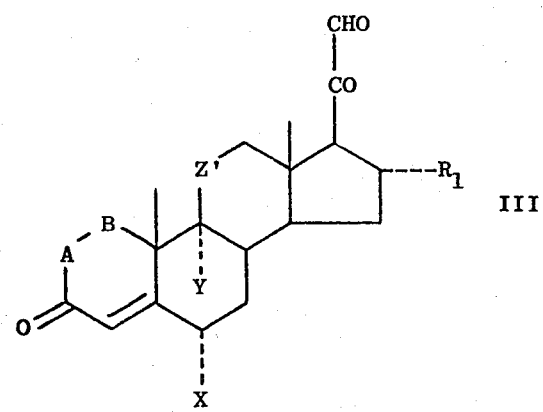

III wherein —A—B—, X, Y, $R_1$ and Z' have the values given above, or a hydrate, hemiacetal or acetal thereof, is oxidized in the presence of an alcohol and cyanide ions with an oxidizing heavy metal oxide, any free hydroxy group in the 11-position being oxidized or esterified, and, optionally thereafter, a thus-produced 21-ester of general Formula I is saponified or transesterified, or a free acid of general Formula I is converted into a salt thereof or is esterified; or c. a compound of general Formula IV

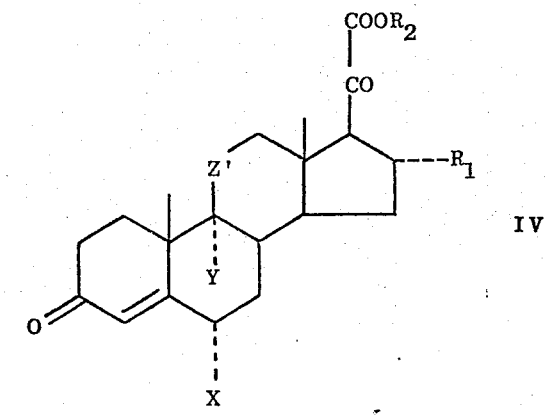

IV wherein X, Y, $R_1$, $R_2$ and Z' have the values given above is dehydrogenated in a conventional manner, to produce a compound of general Formula I wherein —A—B— is —CH═CH—, any free hydroxy group present in the 11-position being oxidized or esterified, and, optionally thereafter, a 21-ester of general Formula I is saponified or transesterified, or a free acid of general Formula I is converted into a salt thereof or is esterified; or d. the hydroxy groups of a compound of general Formula V

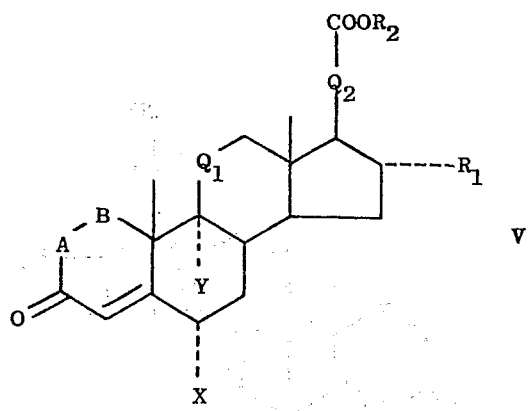

wherein —A—B—, X, Y, $R_1$ and $R_2$ have the values given for Formula I, $Q_1$ is hydroxymethylene, and $Q_2$ is carbonyl or hydroxymethylene, is oxidized in a conventional manner, to produce an 11-keto steroid of general Formula I, and optionally thereafter an ester of general Formula I is saponified or transesterified, or a free acid of general Formula I is converted into a salt thereof or is esterified.

In another composition of matter aspect, this invention relates to pharmaceutically acceptable compositions comprising an anti-inflammatory effective amount per unit dosage of a novel compound of this invention in admixture with a physiologically acceptable carrier adapted for topical application.

In a process aspect, this invention relates to processes for the production of the novel compounds of this invention.

In a method of use aspect, this invention relates to the use of the novel compounds of this invention for the topical treatment of inflammatory conditions.

DETAILED DISCUSSION

Of the compounds of Formula I, preferred subclasses are those wherein:

Ia. When $R_1$ is methyl, $R_2$ is alkyl of 1–12, preferably 1–8 and more preferably 1–4 carbon atoms, and especially methyl or butyl, and when $R_2$ is an alkali metal atom, $R_2$ is a sodium or potassium atom;

Ib. X and Y each are alike or different and each are a fluorine atom or a chlorine atom, especially those of Ia;

Ic. When Z is acyloxymethylene, acyl is preferably that of an alkanoic acid of 1–8 carbon atoms, e.g., formyl, acetyl, propionyl, butyryl, pentanoyl and hexanoyl, especially those of Ia and Ib, preferably of 2–4 carbon atoms.

Id. —A—B— is —CH═CH—, especially those of Ia, Ib and Ic;

Ie. $R_1$ is methyl, especially those of Ib, Ic and Id;

If. Z is carbonyl, especially those of Ia, Ib, Ic, Id and Ie;

Ig. $R_1$ is methyl, $R_2$ is a hydrogen atom, a sodium atom, or saturated unsubstituted hydrocarbon of 1–8 carbon carbon atoms, —A—B— is —CH═CH—, X and Y each are a hydrogen atom or a fluorine atom, and Z is carbonyl or β-alkanoyloxymethylene, e.g., of 2–4 carbon atoms in the alkanoyl group.

Because activity resides in the pregnanoic acid steroidal structure, esters of the free acid also possess the utility of the free acid and its salts. Thus, —COOR$_2$ can also represent an ester group.

For example, $R_2$ can be any hydrocarbon group of 1–18, preferably 1–12, carbon atoms. The hydrocarbon group can be aliphatic, e.g., alkyl or cycloaliphatic, preferably monocyclic, and can be saturated or unsaturated, substituted or unsubstituted; aryl; aralkyl; or alkaryl.

Examples of saturated aliphatic $R_2$ groups are alkyl of 1–12, preferably 1–8, more preferably 1–4 carbon atoms, e.g., methyl, ethyl, propyl, isopropyl, n-butyl and tert.-butyl. Examples of unsaturated aliphatic are vinyl, allyl, propenyl, propynyl, butenyl and butyryl.

Examples of cycloalkyl are those containing 3–12, preferably 5 or 6 ring carbon atoms, e.g., cyclopropyl, cyclopentyl, cyclohexyl, cyclopentyl, cyclopentadienyl and p-dicyclohexyl.

Examples of aryl are mono and dicyclic of up to 12 carbon atoms, e.g., phenyl, and p-diphenyl.

Examples of alkaryl are tolyl, xylyl, ethylphenyl and sym.-diethylphenyl. Examples of aralkyl are benzyl, phenethyl, α-phenylpropyl and diphenylmethyl.

In addition or alternatively to being unsaturated, when $R_2$ is hydrocarbon the hydrocarbon group can bear 1, 2, 3 or more simple substituents, preferably one, since such substituents ordinarily do not affect the overall activity of the parent pregnanoic acid. Examples of such simple substituents are hydroxy, halo, e.g., Cl or F, $NO_2$, sulfato and alkali-metal salts thereof, amido, lower-alkoxy, i.e., containing 1–4 carbon atoms, e.g., methoxy, ethoxy, propoxy, butoxy and tert.-butoxy group; carboxy, the alkali-metal, e.g., sodium and potassium salts thereof and lower-alkyl esters thereof, e.g., carbomethoxy, carboethoxy; amino groups and the pharmaceutically acceptable acid addition salts thereof, e.g., primary amino, mono- and di-lower-alkylamino, e.g., methylamino, dimethylamino, ethylamino, diethylamino, methyl, ethylamino, propylamino, butylamino and the pharmaceutically acceptable acid addition salts thereof.

The acid addition salts are preferably those of the strong mineral acids, e.g., hydrochlorides, hydrobromides, sulfates and phosphates, and the polybasic or hydroxy acids, e.g., oxalates, maleates, citrates and tartrates and any other pharmaceutically acceptable acid.

Examples of preferred $R_2$ groups are methyl, carboxymethyl, ethyl, 2-hydroxyethyl, 2-methoxyethyl, 2-aminoethyl, 2-dimethylaminoethyl, 2-carboxyethyl, propyl, allyl, cyclopropyl, isopropyl, 3-hydroxypropyl, propynyl, 3-aminopropyl, butyl, sec.-butyl, tert.-butyl, 2-butyl, pentyl, isopentyl, tert.-pentyl, 2-methylbutyl, cyclopentyl, hexyl, cyclohexyl, cyclohex-2-enyl, cyclopentylmethyl, heptyl, benzyl, 2-phenylethyl, octyl, bornyl, isobornyl, menthyl, nonyl, decyl, 3-phenylpropyl, 3-phenylprop-2-enyl, dodecyl, tetradecyl, hexadecyl and octadecyl.

The oxidation of the 20-hydroxy group of compounds of general Formula II can be accomplished with an oxidizing agent customarily used for the oxidation of such groups. Suitable oxidizing substances are oxidizing oxides of polyvalent metals, for example, manganese(IV) oxide and lead(IV) oxide.

The process of this invention according to variation (a) can be conducted in those inert solvents usually employed in the steroid chemistry in oxidation reactions. Suitable solvents are, for example, hydrocarbons, such as cyclohexane, benzene, toluene, or xylene; chlorinated hydrocarbons, such as methylene chloride, chloroform, carbon tetrachloride, tetrachloroethylene or chlorobenzene; ethers, such as diethyl ether, diisopropyl ether, dibutyl ether, tetrahydrofuran, dioxane, glycol dimethyl ether or anisole; ketones, such as acetone, methyl ethyl ketone, methyl isobutyl ketone, or acetophenone; or alcohols, such as methanol, ethanol, isopropanol, tert.-butanol, or water. The oxidation can also be conducted in mixtures of the above-mentioned solvents.

The starting compounds of process variation (a) can be produced from the corresponding 21-hydroxy-20-oxopregnane derivatives of general Formula VI

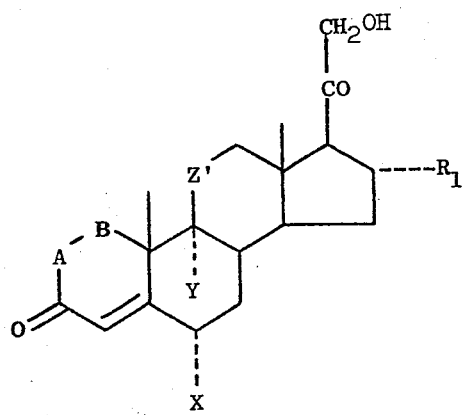

VI wherein —A—B—, X, Y, $R_1$ and Z' have the values given above.

For this purpose, a compound of Formula I is dissolved in an alcohol, the solution is combined with copper(II) acetate, and the mixture is agitated for several days at room temperature. Then, the mixture is combined with aqueous ammonia, extracted, for example, with methylene chloride, the organic phase washed with water, dried and concentrated under vacuum, thus obtaining a crude product consisting of a mixture of the 20α- and 20β-hydroxy steroids. This mixture can be used without further purification as the starting substance for the process of this invention according to variation (a).

Suitable oxidizing heavy metal oxides for the process according to variation (b) are, for example, silver oxide, lead(IV) oxide, minium vanadium(V) oxide and manganese(IV) oxide. The reaction is conducted preferably by employing 0.5 – 50 g., and especially 1–10 g., of heavy metal oxide per gram of compound III.

For this process variation, preferred alcohols are lower or intermediate, primary or secondary alcohols of 1–8 carbon atoms. Examples of such alcohols are methanol, ethanol, propanol, isopropanol, butanol, isobutanol, sec.-butanol, amyl alcohol, isoamyl alcohol, hexanol, heptanol and octanol. These alcohols can also be used simultaneously as the solvents. However, it is of course also possible to employ an inert solvent in addition to the alcohol. Examples of such inert solvents are hydrocarbons, e.g., benzene, cyclohexane and toluene; chlorinated hydrocarbons, e.g., methylene chloride, chloroform and tetrachloroethane; ethers, e.g., diethyl ether, diisopropyl ether, dibutyl ether, glycol dimethyl ether, dioxane and tetrahydrofuran; and dipolar aprotic solvents, such as dimethylformamide, N-methylacetamide and N-methylpyrrolidone.

When conducting the process in accordance with variation (b), a significant increase in the reaction velocity and a pronounced increase in the yield are obtained by conducting this reaction step employing cyanide ions as the catalyst. Reagents yielding cyanide ions are preferably alkali cyanides, e.g., sodium and potassium cyanide. Preferably, 0.01 mole to 10 moles and especially 0.1 mole to 1.0 mole of cyanide is utilized per mole of compound III. When using alkali cyanides as the reagents yielding cyanide ions, the reaction is suitably conducted by adding to the reaction mixture an amount of a mineral acid (such as, for example, sulfuric acid, phosphoric acid, or hydrogen chloride), as sulfonic acid (e.g., p-toluenesulfonic acid), or a carboxylic acid (e.g., formic or acetic acid) required to neutralize the alkali cyanide.

In the preferred embodiment of process variation (b), a reaction temperature of −20° C. to +100° C., preferably 0° C. to +50° C., is employed. The reaction time is dependent on the reaction temperature and the selection of the reactants. The average reaction time is 5–120 minutes.

The compounds of general Formula III can also be converted into compounds of general Formula I using an additional oxidizing agent. Thus, it is possible, for example, to use as the oxidizing agent 5,6-dichloro-2,3-dicyanobenzoquinone or triphenyltetrazolium chloride. However, these oxidation methods are substantially more complicated than the process according to variation (b).

The starting substances for process variation (b) can be produced in a simple manner from the corresponding 21-hydroxy steroids of general Formula VI by reacting the latter compounds with a lower alcohol, e.g., methanol, ethanol or butanol, in the presence of copper(II) acetate for 10–120 minutes at room temperature. The compounds obtained after working up the reaction mixture as usual can be employed directly as starting substances for the process of this invention.

It is possible with the aid of process variation (c) to dehydrogenate steroids of general Formula I which are saturated in the 1,2-position to the corresponding $\Delta^{1,4}$-steroids. This dehydrogenation is conducted in the conventional manner. For example, it is possible to effect the chemical dehydrogenation by means of selenium dioxide or a quinone, e.g., 2,3-dichloro-5,6-dicyanobenzoquinone.

When using selenium dioxide, suitable solvents are, for example, tert.-butanol, tert.-amyl alcohol and ethyl acetate. The reaction can be accelerated by adding small amounts of glacial acetic acid and is accomplished by heating the reaction mixture under reflux. The reaction is terminated after about 10–50 hours.

When using 2,3-dichloro-5,6-dicyanobenzoquinone, the reaction is also preferably carried out at the boiling temperature of the solvent employed. Examples of suitable solvents are alcohols, such as ethanol, butanol and tert.-butanol, ethyl acetate, benzene, dioxane and tetrahydrofuran. To accelerate the reaction, a small amount of nitrobenzene or p-nitrophenol can be added. The reaction times range between 5 and 50 hours.

If an alcohol is used as a solvent for the dehydrogenation, it is advantageous to employ an alcohol of the formula $R_2OH$, wherein $R_2$ has the values indicated in Formula I.

The compounds of general Formula IV can also be dehydrogenated employing conventional microbiological reactions. Examples of such microbiological reactions are fermentations with Bacillus lentus or Arthrobacter simplex.

The process of this invention according to variation (d) and the oxidation of the free 11-hydroxy groups, following as an optional measure, can be accomplished using oxidizing agents customarily utilized for the oxidation of 11-hydroxy groups and 20-hydroxy groups. Thus, it is possible, for example, to oxidize hydroxy groups in the 20α- or 20β-position with manganese(IV) oxide or lead(IV) oxide. For this variation of the process, active manganese (IV) oxide is preferably employed, as customary in the steroid chemistry for oxidation reactions, in order to obtain satisfactory yields.

This reaction can be conducted in those inert solvents which are usually employed in the steroid chemistry for oxidation reactions. Suitable solvents are, for example, hydrocarbons, such as cyclohexane, benzene, toluene and xylene; chlorinated hydrocarbons, e.g., methylene chloride, chloroform, carbon tetrachloride, tetrachloroethylene and chlorobenzene; ethers, such as diethyl ether, diisopropyl ether, dibutyl ether, tetrahydrofuran, dioxane, glycol dimethyl ether and anisole; ketones, such as acetone, methyl ethyl ketone, methyl isobutyl ketone and acetophenone; and alcohols, e.g., methanol, ethanol, isopropanol and tert.-butanol. The process of this invention can also be effected in mixtures of the above-mentioned solvents.

It is also possible to oxidize hydroxy groups in the 20α- or 20β-position, as well as hydroxy groups in the 11α- or 11β-position with chromium(VI) oxide. This reaction can be conducted, for example, in the presence of a base, such as pyridine, or in an acidic aqueous solution. If the reaction is carried out in an acidic aqueous solution, it is possible to add to these solutions an inert, water-soluble solvent, e.g., acetone or dimethylformamide. It is also possible to effect the oxidation of the hydroxy groups in an acidic solution using sodium chromate or sodium bichromate.

An 11-position hydroxy can be esterified in a conventional manner. An example of an esterification method which can be employed is the esterification with a carboxylic acid anhydride in the presence of a strong acid, such as, for example, p-toluenesulfonic acid, sulfuric acid, hydrogen chloride or trifluoroacetic acid, or in the presence of a basic esterification catalyst, e.g., 4-dimethylaminopyridine.

The optional 21-ester saponification can be conducted according to conventional modes of operation. One example is saponification in water or aqueous alcohol in the presence of an acidic catalyst, such as hydrochloric acid, sulfuric acid or p-toluenesulfonic acid, or in the presence of a basic catalyst, such as potassium bicarbonate, potassium carbonate, sodium hydroxide or potassium hydroxide.

The optional esterification of the free acids can also be conducted according to known methods. Thus, the acids can be reacted, for example, with diazomethane or diazoethane, thus obtaining the corresponding methyl or ethyl esters. A generally applicable method is the reaction of the acids with an alcohol in the presence of carbonyl diimidazole, dicyclohexylcarbodiimide, or trifluoroacetic acid anhydride. It is also possible, for example, to react the acids with an alkyl halogenide in the presence of copper(I) oxide or silver oxide.

Another method for converting the free acids into the corresponding acid alkyl esters is the use of the corresponding dimethylformamide alkyl acetals. The free acids can also be reacted in the presence of a strongly acidic catalyst, such as hydrogen chloride, sulfuric acid, perchloric acid, trifluoromethylsulfonic acid or p-toluenesulfonic acid, with an alcohol or a lower alkanecarboxylic acid ester of an alcohol. It is also possible to convert the carboxylic acids into their acid chlorides or acid anhydrides and react these in the presence of a basic catalyst with an alcohol.

The carboxylic acid alkali metal salts are produced, for example, during the saponification of the esters employing a basic catalyst or during the neutralization of the acids with an alkali carbonate or alkali hydroxide, e.g., sodium carbonate, sodium bicarbonate, sodium hydroxide, potassium carbonate, potassium bicarbonate or potassium hydroxide.

It is also possible to react esters of the general Formula I with the selected alcohol in the presence of a basic catalyst. In this transesterification reaction, suitable preferred basic catalysts are the alkali, alkaline earth and aluminum alcoholates. This reaction is preferably effected at a reaction temperature of from 0° C. to 180° C. During this reaction, the finally desired alcohol is used in an excess. Preferably, 10 – 1000 moles of alcohol per mole of steroid is used. The alcohol optionally can be diluted with another solvent, such as, for example, an ether, e.g., di-n-butyl ether, tetrahydrofuran, dioxane, glycol dimethyl ether, or a dipolar aprotic solvent, such as dimethylformamide, N-methylacetamide, dimethyl sulfoxide, N-methylpyrrolidone, or acetonitrile. This variation of the reaction is conducted preferably with less than 1 mole of basic catalyst per mole of steroid being utilized, preferably 0.0001 to 0.5 mole per mole of steroid.

Employing the process of the present invention, the following 11-keto compounds of general Formula I can be prepared, for example:

3,11,20-trioxo-1,4-pregnadiene-21-oic acid
3,11,20-trioxo-6α-methyl-4-pregnene-21-oic acid
3,11,20-trioxo-6α-methyl-1,4-pregnadiene-21-oic acid
3,11,20-trioxo-16α-methyl-4-pregnene-21-oic acid
3,11,20-trioxo-16α-methyl-1,4-pregnadiene-21-oic acid
3,11,20-trioxo-6α,16α-dimethyl-4-pregnene-21-oic acid
3,11,20-trioxo-6α,16α-dimethyl-1,4-pregnadiene-21-oic acid
6α-fluoro-3,11,20-trioxo-4-pregnene-21-oic acid
6α-fluoro-3,11,20-trioxo-1,4-pregnadiene-21-oic acid
9α-fluoro-3,11,20-trioxo-4-pregnene-21-oic acid
9α-fluoro-3,11,20-trioxo-1,4-pregnadiene-21-oic acid
6α-fluoro-3,11,20-trioxo-16α-methyl-4-pregnene-21-oic acid 6α-fluoro-3,11,20-trioxo-16α-methyl-1,4-pregnadiene-21-oic acid
9α-fluoro-3,11,20-trioxo-16α-methyl-4-pregnene-21-oic acid
9α-fluoro-3,11,20-trioxo-16α-methyl-1,4-pregnadiene-21-oic acid
6α,9α-difluoro-3,11,20-trioxo-16α-methyl-4-pregnene-21-oic acid
6α,9α-difluoro-3,11,20-trioxo-16α-methyl-1,4-pregnadiene-21-oic acid
6α-fluoro-9α-chloro-3,11,20-trioxo-16α-methyl-4-pregnene-21-oic acid
6α-fluoro-9α-chloro-3,11,20-trioxo-16α-methyl-1,4-pregnadiene-21-oic acid
6α-fluoro-2-chloro-3,11,20-trioxo-16α-methyl-1,4-pregnadiene-21-oic acid
 the sodium salts of these acids,
 the methyl esters of these acids,
 the ethyl esters of these acids,
 the propyl esters of these acids,
 the butyl esters of these acids,
 the pentyl esters of these acids, and
 the hexyl esters of these acids.

The following 11β-acyloxy compounds of general Formula I can be produced, for example, employing the process of this invention:

The 11-formates, 11-acetates, 11-propionates, and 11-butyrates of the following acids:
11β-hydroxy-3,20-dioxo-1,4-pregnadiene-21-oic acid
11β-hydroxy-3,20-dioxo-16α-methyl-4-pregnene-21-oic acid
11β-hydroxy-3,20-dioxo-16α-methyl-1,4-pregnadiene-21-oic acid
6α-fluoro-11β-hydroxy-3,20-dioxo-16α-methyl-4-pregnene-21-oic acid
6α-fluoro-11β-hydroxy-3,20-dioxo-16α-methyl-1,4-pregnadiene-21-oic acid
9α-fluoro-11β-hydroxy-3,20-dioxo-4-pregnene-21-oic acid
9α-fluoro-11β-hydroxy-3,20-dioxo-1,4-pregnadiene-21-oic acid
9α-fluoro-11β-hydroxy-3,20-dioxo-16α-methyl-4-pregnene-21-oic acid
9α-fluoro-11β-hydroxy-3,20-dioxo-16α-methyl-1,4-pregnadiene-21-oic acid
11β-hydroxy-3,20-dioxo-6α,16α-dimethyl-4-pregnene-21-oic acid
11β-hydroxy-3,20-dioxo-6α,16α-dimethyl-1,4-pregnadiene-21-oic acid
6α,9α-difluoro-11β-hydroxy-3,20-dioxo-16α-methyl-4-pregnene-21-oic acid
6α,9α-difluoro-11β-hydroxy-3,20-dioxo-16α-methyl-1,4-pregnadiene-21-oic acid
6α-fluoro-9α-chloro-11β-hydroxy-3,20-dioxo-16α-methyl-4-pregnene-21-oic acid
6α-fluoro-9α-chloro-11β-hydroxy-3,20-dioxo-16α-methyl-1,4-pregnadiene-21-oic acid
6α-fluoro-2-chloro-11β-hydroxy-3,20-dioxo-16α-methyl-1,4-pregnadiene-21-oic acid,
 and furthermore the sodium salts,
 the methyl esters,
 the ethyl esters,
 the propyl esters,
 the butyl esters,
 the pentyl esters, and
 the hexyl esters of these acids.

Also, it is possible, employing the process of this invention to prepare, for example, the following compounds of general Formula I, unsubstituted in the 11-position:
3,20-dioxo-1,4-pregnadiene-21-oic acid
3,20-dioxo-6α-methyl-4-pregnene-21-oic acid
3,20-dioxo-6α-methyl-1,4-pregnadiene-21-oic acid
3,20-dioxo-16α-methyl-4-pregnene-21-oic acid
3,20-dioxo-16α-methyl-1,4-pregnadiene-21-oic acid
3,20-dioxo-6α,16α-dimethyl-4-pregnene-21-oic acid
3,20-dioxo-6α,16α-dimethyl-1,4-pregnadiene-21-oic acid
6α-fluoro-3,20-dioxo-4-pregnene-21-oic acid
6α-fluoro-3,20-dioxo-1,4-pregnadiene-21-oic acid
6α-fluoro-3,20-dioxo-16α-methyl-4-pregnene-21-oic acid
6α-fluoro-3,20-dioxo-16α-methyl-1,4-pregnadiene-21-oic acid
6α-fluoro-2-chloro-3,20-dioxo-16α-methyl-1,4-pregnadiene-21-oic acid,
 as well as the sodium salts,
 the methyl esters,
 the ethyl esters,
 the propyl esters,
 the butyl esters,
 the pentyl esters, and
 the hexyl esters of these acids.

The compounds of general Formula I are valuable medicinal agents and valuable intermediates for the preparation of medicinal agents.

The pharmacologically effective compounds of general Formula I possess, upon local administration, an excellent antiphlogistic effectiveness and moreover have the advantage that they are essentially inactive systemically.

The novel compounds are suitable, in combination with the vehicles customary in galenic pharmacy, for the local treatment of contact dermatitis, eczemas of a great variety of types, neurodermitis, erythrodermia, burns, pruritus vulvae et ani, rosacea, erythematodes cutaneus, psoriasis, lichen ruber planus et verrucosus, and similar skin diseases.

The special medicinal agents are prepared in the usual manner by converting the effective agents with suitable additives into the desired form of application, such as, for example: solutions, lotions, ointments, creams, or plasters. In the thus-formulated medicinal agents, the effective agent concentration is dependent on the form of application. In case of lotions and ointments, a concentration of effective agent is 0.001% to 1% is preferably utilized.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. A solution of 10.0 g. of 6 α-fluoro-21-hydroxy-16 α-methyl-1,4-pregnadiene-3,11,20-trione in 500 ml. of butanol is combined with 5.0 g. of copper(II) acetate in 500 ml. of butanol. The solution is agitated for 10 days at room temperature, then clarified by filtering, and concentrated under vacuum. The residue is taken up in methylene chloride, the solution is washed with 10% ammonium hydroxide solution and water, dried, and concentrated. The residue is chromatographed on silica gel. With 5–6% acetone/hexane, after recrystallization from acetone/hexane, one produces 1.23 g. of the butyl ester of 6 α-fluoro-20 α-hydroxy-3,11-dioxo-16 α-methyl-1,4-pregnadiene-21-oic acid, m.p. 154.9°C. $[\alpha]_D^{25} = +70°$ (chloroform). UV: $\epsilon_{237} = 15,900$ (methanol).

With 8–12% acetone/hexane, after recrystallization from acetone/hexane, one obtains 2.59 g. of the butyl ester of 6 α-flouro-20β-hydroxy-3,11-dioxo-16 α-methyl-1,4-pregnadiene-21-oic acid, m.p. 153.7°c. $[\alpha]_D^{25} = +82°$ (chloroform). UV: $\epsilon_{238}$ 32 16,000 (methanol).

b. 1.0 g. of the butyl ester of 6 α-fluro-20α-hydroxy-3,11-dioxo-16α-methyl-1,4-pregnadiene-21-oic acid is dissolved in 20 ml. of methylene chloride; the solution is combined with 10 g. of active manganese (IV) oxide, and the mixture is agitated for 3 hours at room temperature. Thereafter, the mixture is filtered off from excess manganese dioxide, the filtrate is evaporated, and the residue is recrystallized from acetone/hexane. Yield: 670 mg. of the butyl ester of 6 α-fluro-3,11,20-trioxo-16 α-methyl-1,4-pregnadiene-21-oic acid, m.p. 106.3° C. $[\alpha]_D^{25} = +190°$ (chloroform). UV: $\epsilon_{238} = 16,500$ (methanol).

c. 500 mg. of the butyl ester of 6α-fluro-20β-hydroxy-3,11-dioxo-16α-methyl-1,4-pregnadiene-21-oic acid is dissolved in 20 ml. of acetone and combined at 0° C. with 0.5 ml. of Jones reagent (26.72 g. of chromium(VI) oxide is dissolved in 23 ml. of concentrated sulfuric acid, and the solution is filled up with water to 100 ml.). After a reaction time of 25 minutes, the mixture is stirred into 250 ml. of saturated aqueous sodium chloride solution. The thus-precipitated product is isolated and recrystallized from acetone/hexane. Yield: 351 mg. of the butyl ester of 6α-fluoro-3,11,20-trioxo-16α-methyl-1,4-pregnadiene-21-oic acid, m.p. 105° C. $[\alpha]_D^{25} = +187°$ (chloroform).

EXAMPLE 2 a. A solution of 11.3 g. of 6α-fluoro-11β, 21-dihydroxy-16α-methy-1,4-pregnadiene-3,20-dione in 500 ml. of absolute methanol is combined with 3.0 g. of copper(II) acetate in 500 ml. of absolute methanol. The solution is agitated for 170 hours at room temperature, then filtered to clarify the solution, and concentrated under vacuum. The residue is mixed with 10% ammonium hydroxide solution and extracted with methylene chloride. The organic phase is washed repeatedly with water, dried over sodium sulfate, and concentrated under vacuum. The residue is chromatographed on 1.3 kg. of silica gel, 6–7% acetone/methylene chloride yields after recrystallization from acetone/hexane 1.40 g. of the methyl ester of 6α-fluoro-11 β,20αdihydroxy-3-oxo-16α-methyl-1,4-pregnadiene-21-oic acid, m.p. 191°–192°C. $[\alpha]_D^{25} = 0°$ (chloroform). UV: $\epsilon_{243} = 15,700$ (methanol). Elution with 8–10% acetone/methylene chloride and recrystallizing twice from acetone/hexane, yields 2.9 g. of the methyl ester of 6α-fluoro-11 β,20β-dihydroxy-3-oxo-16α-methyl-1,4-pregnadiene-21-oic acid, m.p. 128°–130°C. $[\alpha]_D^{25} = +22°$ (chloroform). UV: $\epsilon_{242} = 15,200$ (methanol).

b. A solution of 1.0 g. of the methyl ester of 6α-fluoro-11 β,20β-dihydroxy-3-oxo-16α-methyl-1,4-pregnadiene-21-oic acid in 50 ml. of acetone is combined at 0° C. with 1.0 ml. of Jones reagent. After 30 minutes, the reaction product is mixed with saturated sodium chloride solution, extracted with methylene chloride, the extract is concentrated, and the residue is recrystallized from acetone/hexane, thus obtaining 691 mg. of the methyl ester of 6α-fluoro-3,11,20-trioxo-16α-methyl-1,4-pregnadiene-21-oic acid, m.p. 193.4° C. $[\alpha]_D^{25} = +191°$ (chloroform). UV: $\epsilon_{238} = 16,400$ (methanol).

EXAMPLE 3 a. 2.1 g. of a mixture of the methyl ester of 6α-fluoro-11 β,20α-dihydroxy-3-oxo-16α-methyl-1,4-pregnadiene-21-oic acid and the methyl ester of 6α-fluoro-11 β,20β-dihydroxy-3-oxo-16α-methyl-1,4-pregnadiene-21-oic acid is dissolved in 20 ml. of methylene chloride; the solution is mixed with 20 g. of active manganese(IV) oxide ("active precipitate for synthesis purposes" manufactured by Merck A.G.) and refluxed for 6 hours. Thereafter, the product is filtered off from the manganese(IV) oxide, the filtrate is evaporated, and the residue is recrystallized from acetone/hexane, thus obtaining 450 mg. of the methyl ester of 6α-fluoro-11 β-hydroxy-3,20-dioxo-16α-methyl-1,4-pregnadiene-21-oic acid, m.p. 182°–184°c. $[\alpha]_D^{25} = +144°$ (chloroform). UV: $\epsilon_{242} = 17,000$ (methanol).

b. 5.0 g. of the methyl ester of 6α-fluoro-11β-hydroxy-3,20-dioxo-16α-methyl-1,4-pregnadiene-21-oic acid is dissolved in 300 ml. of absolute ethanol and combined with 250 mg. of potassium tert.-butylate. The mixture is refluxed under argon for one hour. The reaction product is precipitated with 1% strength acetic acid, and the precipitate is vacuum-filtered. The crystalline crude product is taken up in 100 ml. of methylene chloride, washed with saturated sodium bicarbonate solution and with water, and the solution is dried with sodium sulfate and freed of the solvent under vacuum. By recrystallization of the crude product from acetone/hexane, 2.30 g. of the ethyl ester of 6α-fluoro-11β-hydroxy-3,20-dioxo-16α-methyl-1,4-pregnadiene-21-oic acid is obtained, m.p. 183° C. $[\alpha]_D^{25}$ 32 + 143° (chloroform).

c. A solution of 500 mg. of the ethyl ester of 6α-fluoro-11β-hydroxy-3,20-dioxo-16α-methyl-1,4-pregnadiene-21-oic acid in 20 ml. of acetone is combined at 0° C with 0.5 ml. of Jones reagent. After a reaction period of 25 minutes, the mixture is poured into 250 ml. of ice water saturated with sodium chloride. The precipitated product is filtered off and dissolved in methylene chloride. The solution is washed with sodium bicarbonate solution and water, dried over sodium sulfate, and evaporated under vacuum. The residue is recrystallized from acetone/hexane, thus obtaining 400 mg. of the ethyl ester of 6α-fluoro-3,11,20-trioxo-16α-methyl-1,4-pregnadiene-21-oic acid, m.p. C. $[\alpha]_D^{25} = +195°$ (chloroform). UV: $\epsilon_{238} = 16,500$ (methanol).

EXAMPLE 4 a. 5.0 g. of the butyl ester of 6α-fluoro-11β-hydroxy-3,20-dioxo-16α-methyl-1,4-pregnadiene-21-oic acid is reacted, as described in Example 3(b), with n-propanol and worked up. After recrystallization from acetone/hexane, the product is 2.0 g. of the propyl ester of 6α-fluoro-11β-hydroxy-3,20-dioxo-16α-methyl-1,4-pregnadiene-21-oic acid, m.p. 180° C. $[\alpha]_D^{25} = +140°$ (chloroform).

b. 500 mg. of the propyl ester of 6α-fluoro-11β-hydroxy-3,20-dioxo-16α-methyl-1,4-pregnadiene-21-oic acid is oxidized with Jones reagent as set forth in Example 3(c). The crude product, recrystallized from acetone/hexane, yields 254 mg. of the propyl ester of 6α-fluoro-3,11,20-trioxo-16α-methyl-1,4-pregnadiene- 21-oic acid, m.p. 114.4° C. $[\alpha]_D^{25} = +198°$ (chloroform). UV: $\epsilon_{237} = 16,700$ (methanol).

EXAMPLE 5 a. 1.0 g. of 6α-fluoro-21-hydroxy-16α-methyl-1,4-pregnadiene-3,11,20-trione is dissolved in 125 ml. of methanol, and the solution is combined with a solution of 250 mg. of copper(II) acetate in 125 ml. of methanol. The mixture is stirred for 30 minutes at room temperature while passing atmospheric oxygen therethrough, then diluted with methylene chloride, washed with 5% ammonium chloride solution and water, dried over sodium sulfate, and the solvent evaporated under vacuum. Yield: 1.1 g. of 6α-fluoro-3,11,20-trioxo-16α-methyl-1,4-pregnadien-21-al as a crude product.

b. The thus-obtained product is dissolved in 50 ml. of isopropyl alcohol, and the solution is agitated, after adding 150 mg. of potassium cyanide, 1.0 ml. of acetic acid, and 2 g. of manganese(IV) oxide, at room temperature for 30 minutes. The manganese(IV) oxide is filtered off, the filtrate diluted with methylene chloride, washed with water, dried, and concentrated to dryness. The residue is chromatographed on silica gel. After recrystallizationn from acetone/hexane, the product is 653 mg. of the isopropyl ester of 6α-fluoro-3,11,20-trioxo-16α-methyl-1,4-pregnadiene-21-oic acid, m.p. 152.8° C. $[\alpha]_D^{25} = +188°$ (chloroform). UV: $\epsilon_{238} = 16,600$ (methanol).

EXAMPLE 6 a. Under the reaction conditions set forth in Example 2(a), but using tert.-butanol as the solvent, one obtains from 20 g. of 6α-fluoro-11 β,21-dihydroxy-16α-methyl-1,4-pregnadiene-3,20-dione, 9.8 g. of a mixture of the tert.-butyl ester of 6α-fluoro-11 β,20α-dihydroxy-3-oxo-16α-methyl-1,4-pregnadiene-21-oic acid and the tert.-butyl ester of 6α-fluoro-11β,20β-dihydroxy-3-oxo-16α-methyl-1,4-pregnadiene-21-oic acid.

b. The thus-obtained mixture is converted, as described in Example 3(a), into the tert.-butyl ester of 6α-fluoro-11β-hydroxy-3,20-dioxo-16α-methyl-1,4-pregnadiene-21-oic acid. Yield: 3.16 g. (from hexane/acetone), m.p. 175°–176° C. $[\alpha]_D^{25} = +127°$ (chloroform).

c. 500 mg. of the tert.-butyl ester of 6α-fluoro-11β-hydroxy-3,20-dioxo-16α-methyl-1,4-pregnadiene-21-oic acid is oxidized with Jones reagent as described in Example 3(c), thus obtaining 371 mg. of the tert.-butyl ester of 6α-fluoro-3,11,20-trioxo-16α-methyl-1,4-pregnadiene-21-oic acid, m.p. 180.1° C. $[\alpha]_D^{25} = +172°$ (chloroform). UV: $\epsilon_{238} = 16,400$ (methanol).

EXAMPLE 7

5.0 g. of 6α-fluoro-21-hydroxy-16α-methyl-1,4-pregnadiene-3,11,20-trione is reacted as set forth in Example 1(a) but in 1,1-dimethylpropanol as the solvent. The crude product is oxidized with Jones reagent as described in Example 1(c). After chromatography on silica gel and after recrystallization from acetone/hexane, the yield is 1.21 g. of the (1,1-dimethylpropyl) ester of 6α-fluoro-3,11,20-trioxo-16α-methyl-1,4-pregnadiene-21-oic acid, m.p. 159.3° C. $[\alpha]_D^{25} = +170°$ (chloroform). UV: $\epsilon_{238} = 16,400$ (methanol).

EXAMPLE 8 a. 5.0 g. of the methyl ester of 6α-fluoro-11β-hydroxy-3,20-dioxo-16α-methyl-1,4-pregnadiene-21-oic acid is dissolved in 250 ml. of isopentanol and mixed with 250 mg. of potassium tert.-butylate. The solution is heated under argon for 1 hour to 100° C., then diluted with the same volume of methylene chloride, washed with 1% acetic acid and water, the organic solution is dried with sodium sulfate, and the solvents are distilled off under vacuum. The crude product is chromatographed with hexane/acetone on 500 g. of silica gel and recrystallized from acetone/hexane, thus obtaining 1.75 g. of the 3-methylbutyl ester of 6α-fluoro-11β-hydroxy-3,20-dioxo-16α-methyl-1,4-pregnadiene-21-oic, m.p. 192° C. $[\alpha]_D^{25} = +135°$ (chloroform).

b. As described in Example 3(c), 500 mg. of the 3-methylbutyl ester of 6α-fluoro-11β-hydroxy-3,20-dioxo-16α-methyl-1,4-pregnadiene-21-oic acid is oxidized, worked up, and recrystallized from acetone/hexane, thus obtaining 121 mg. of the 3-methylbutyl ester of 6α-fluoro-3,11,20-trioxo-16α-methyl-1,4-pregnadiene-21-oic acid, m.p. 113.7°C. $[\alpha]_D^{25} = +182°$ (chloroform). UV: $\epsilon_{237} = 16,700$ (methanol).

EXAMPLE 9 a. 10.5 g. of 6α-fluoro-11 β,21-dihydroxy-16α-methyl-1,4-pregnadiene-3,20-dione is reacted with cyclohexanol under the conditions set forth in Example 2(a), thus obtaining a mixture of the cyclohexyl ester of 6α-fluoro-11 β,20α-dihydroxy-3-oxo-16α-methyl-1,4-pregnadiene-21-oic acid and the cyclohexyl ester of 6α-fluoro-11β,20α-dihydroxy-3-oxo-16α-methyl-1,4-pregnadiene-21-oic acid.

b. 5.1 g. of this mixture is oxidized as disclosed in Example 3(a), thus producing 1.35 g. of the cyclohexyl ester of 6α-fluoro-11β-hydroxy-3,20-dioxo-16α-methyl-1,4-pregnadiene-21-oic acid, m.p. 258–260° C. $[\alpha]_D^{25} = +130°$ (dioxane).

c. 500 mg. of the cyclohexyl ester of 6α-fluoro-11β-hydroxy-3,20-dioxo-16α-methyl-1,4-pregnadiene-21-oic acid is oxidized with Jones reagent as described in Example 3(c), thus obtaining 451 mg. of the cyclohexyl ester of 6α-fluoro-3,11,20-trioxo-16α-methyl-1,4-pregnadiene-21-oic acid in the form of an amorphous powder. $[\alpha]_D^{25} = +179°$ (chloroform). UV: $\epsilon_{237} = 16,600$ (methanol).

EXAMPLE 10 a. 1.0 g. of the methyl ester of 6α-fluoro-11β-hydroxy-3,20-dioxo-16α-methyl-1,4-pregnadiene-21-oic acid is dissolved in 10 ml. of tetrahydrofuran and 10 ml. of methylene chloride, mixed with 2 g. of N-chlorosuccinimide and 2 ml. of dioxane saturated with hydrogen chloride, and stored for 20 minutes at room temperature. Then, the reaction mixture is poured into water, the thus-separated product is extracted with chloroform, and the chloroform phase is evaporated to dryness under vacuum.

The residue is dissolved in 10 ml. of pyridine, the solution is heated for 2 hours to 60° C. and then poured into 1N aqueous hydrochloric acid, and the reaction mixture is extracted with methylene chloride. The methylene chloride phase is washed and concentrated under vacuum. The crude product is chromatographed by means of a hexane/acetone gradient over 100 g. of silica gel. After recrystallization from acetone/hexane, the product is 385 mg. of the methyl ester of 6α-fluoro-2-chloro-11β-hydroxy-3,20-dioxo-16α-methyl-1,4-pregnadiene-21-oic acid, m.p. 208° C.

b. As described in Example 3(c), 500 mg. of the methyl ester of 6α-fluoro-2-chloro-11β-hydroxy-3,20-dioxo-16α-methyl-1,4-pregnadiene-21-oic acid is oxidized with Jones reagent and worked up. The crude product is recrystallized from acetone/hexane thus obtaining 430 mg. of the methyl of 6α-fluoro-2-chloro-3,11,20-trioxo-16α-methyl-1,4-pregnadiene-21-oic acid, m.p. 180.0°C. $[\alpha]_D^{25} = +162°$ (chloroform). UV: $\epsilon_{244} = 14,600$ (methanol).

EXAMPLE 11 a. Under the reaction conditions described in Example 2(a), there is obtained from 16.0 g. of 6α-fluoro-9α-chloro-11β,21-dihydroxy-16α-methyl-1,4-pregnadiene-3,20-dione, 15.4 g. of a mixture of the methyl ester of 6α-fluoro-9α-chloro-11β,20α-dihydroxy-3-oxo-16α-methyl-1,4-pregnadiene-21-oic acid and the methyl ester of 6α-fluoro-9α-chloro-11β,20β-dihydroxy-3-oxo-16α-methyl-1,4-pregnadiene-21-oic acid.

b. 12.9 g. of the thus-obtained mixture is converted, as described in Example 1(b), into 5.40 g. of the methyl ester of 6α-fluoro-9α-chloro-11β-hydroxy-3,20-dioxo-16α-methyl-1,4-pregnadiene-21-oic acid, m.p. 226°–228°C. $[\alpha]_D^{25} = +154°$ (dioxane).

c. A solution of 1.0 g. of the methyl ester of 6α-fluoro-9α-chloro-11β-hydroxy-3,20-dioxo-16α-methyl-1,4-pregnadiene-21-oic acid in 60 ml. of acetone is combined with 1.0 ml. of Jones reagent and agitated for 2.5 hours at room temperature. The reaction mixture is poured into 500 ml. of ice water saturated with sodium chloride; the thus-precipitated product is isolated and dissolved in methylene chloride. The solution is washed with sodium bicarbonate solution and water, dried over sodium sulfate, and concentrated under vacuum. The residue is recrystallized from acetone/hexane, thus obtaining 870 mg. of the methyl ester of 6α-fluoro-9α-chloro-3,11,20-trioxo-16α-methyl-1,4-pregnadiene-21-oic acid, m.p. 238.9° c. $[\alpha]_D^{25} = +258°$ (chloroform). UV: $\epsilon_{235} = 16,800$ (methanol).

EXAMPLE 12 a. 16.0 g. of 6α,9α-difluoro-11β,21-dihydroxy-16α-methyl-1,4-pregnadiene-3,20-dione, 8 g. of copper(II) acetate, and 1000 ml. of methanol are reacted as set forth in Example 2(a), worked up, and chromatographed. With 6–8% acetone/methylene chloride, and after a single recrystallization from hexane/acetone, the product thus obtained is 1.1 g. of the methyl ester of 6α,9α-difluoro-11β,20α-dihydroxy-3-oxo-16α-methyl-1,4-pregnadiene-21-oic acid, m.p. 174° C. $[\alpha]_D^{25} = +21°$ (dioxane). UV: $\epsilon_{238} = 16,400$ (methanol).

With 9–11% acetone/methylene chloride, after recrystallization from acetone/hexane, the product is 5.3 g. of the methyl ester of 6α,9α-dilfuoro-11β,20β-dihydroxy-3-oxo-16α-methyl-1,4-pregnadiene-21-oic acid, m.p. 236° C. $[\alpha]_D^{25} = +17°$ (dioxane). UV: $\epsilon_{236}$ 32 16,900 (methanol).

b. 12.1 g. of a mixture of the methyl ester of 6α,9α-difluoro-11β,20α-dihydroxy-3-oxo-16α-methyl-1,4-pregnadiene-21-oic acid and the methyl ester of 6α,9α-difluoro-11β,20β-dihydroxy-3-oxo-16α-methyl-1,4-pregnadiene-21-oic acid is mixed with 200 ml. of acetone, 200 ml. of methylene chloride, and 350 g. of active manganese(IV) oxide. After 3 hours of agitation, the reaction mixture is filtered off from the manganese(IV) oxide, the solvent is evaporated, and the crude product is recrystallized twice from acetone/hexane, thus obtaining 5.1 g. of the methyl ester of 6α,9α-difluoro-11β-hydroxy-3,20-dioxo-16α-methyl-1,4-pregnadiene-21-oic acid, m.p. 207°–208° C. $[\alpha]_D^{25} = 128°$ (dioxane). UV: $\epsilon_{236} = 17,000$ (methanol).

c. 500 mg. of the methyl ester of 6α,9α-difluoro-11β-hydroxy-3,20-dioxo-16α-methyl-1,4-pregnadiene-21-oic acid is oxidized with Jones reagent as described in Example 11(c), worked up, and the product thus obtained is 420 mg. of the methyl ester of 6α,9α-difluoro-3,11,20-trioxo-16α-methyl-1,4-pregnadiene-21-oic acid (from acetone/hexane), m.p. 164.9° C. $[\alpha]_D^{25} = +166°$ (chloroform). UV: $\epsilon_{234} = 16,900$ (methanol).

EXAMPLE 13 a. 4.0 g. of the methyl ester of 6α-fluoro-9α-chloro-11β-hydroxy-3,20-dioxo-16α-methyl-1,4-pregnadiene-21-oic acid is converted into the butyl ester under the conditions set forth in Example 8(a), but in butanol as the solvent. The crude product is chromatographed on silica gel with an acetone/hexane gradient. After recrystallization from acetone/hexane, 2.2 g. of the butyl ester of 6α-fluoro-9α-chloro-11β-hydroxy-3,20-dioxo-16α-methyl-1,4-pregnadiene-21-oic acid is obtained, m.p. 180.8° C. $[\alpha]_D^{25} = +150°$ (chloroform). UV: $\epsilon_{238} = 16,900$ (methanol).

b. 2.0 g. of the butyl ester of 6α-fluoro-9α-chloro-11β-hydroxy-3,20-dioxo-16α-methyl-1,4-pregnadiene-21-oic acid is mixed with 50 ml. of butanol and 2.5 g. of potassium acetate. The mixture is refluxed for 2 hours.

Then, the mixture is combined, after cooling, with 100 ml. of chloroform, the chloroform phase is washed with water and concentrated to dryness under vacuum. Yield: 1.62 g. of the butyl ester of 6α-fluoro-9,11β-epoxy-3,20-dioxo-16α-methyl-1,4-pregnadiene-21-oic acid as a crude product.

c. The thus-obtained crude product is introduced into a mixture, cooled to −50° C., consisting of 5.0 ml. of dimethylformamide and 5.0 ml. of anhydrous hydrofluoric acid, and stored for 4 days at room temperature.

Thereafter, the mixture is poured into 500 ml. of 10% aqueous potassium bicarbonate solution, extracted with methylene chloride, the methylene chloride phase is concentrated under vacuum, and the residue is purified by chromatography over a silica gel column. Yield: 380 mg. of the butyl ester of 6α,9α-difluoro-11β-hydroxy-3,20-dioxo-16β-methyl-1,4-pregnadiene-21-oic acid.

d. 500 mg. of the butyl ester of 6α,9α-difluoro-11β-hydroxy-3,20-dioxo-16α-methyl-1,4-pregnadiene-21-oic acid is oxidized as indicated in Example 11(c), worked up, and recrystallized from acetone/hexane. Yield: 145 mg. of the butyl ester of 6α,9α-difluoro-3,11,20-trioxo-16α-methyl-1,4-pregnadiene-21-oic acid, m.p. 95.9° C. $[\alpha]_D^{25} = +155°$ (chloroform). UV: $\epsilon_{234} = 17,000$ (methanol).

EXAMPLE 14 a. 107.0 g. of 9α-fluoro-11β,17α,21-trihydroxy-16α-methyl-1,4-pregnadiene-3,20-dione is dissolved in 2 liters of glacial acetic acid and combined with 10.0 g. of zinc acetate containing water of crystallization. The reaction mixture is refluxed for 4 hours and then precipitated with 10 liters of ice water. The precipitate is filtered off and taken up in methylene chloride which is then washed neutral with water. The solvent is dried over anhydrous sodium sulfate and evaporated under vacuum. Yield: 112.0 g. of a mixture of 9α-fluoro-11β,20-dihydroxy-3-oxo-16α-methyl-1,4,17(20)-pregnatrien-21-al and 9α-fluoro-11β-hydroxy-20-acetoxy-3-oxo-16α-methyl-1,4,17-(20)-pregnatrien-21-al as a viscous oil.

b. 108.0 g. of the above-mentioned mixture is dissolved in 3 liters of methanol and combined with a solution of 15.0 g. of potassium hydroxide in 30 ml. of water. Under argon, the mixture is heated for 1½ hours under reflux, and then the methanol is distilled off under vacuum. The residue is taken up in 2 liters of water and 2 liters of methylene chloride and, for further purification, the aqueous phase is repeatedly extracted with methylene chloride. The aqueous solution is acidified with 4N sulfuric acid and again extracted several times with methylene chloride; the latter is then dried over sodium sulfate. After the solvent has been evaporated under vacuum, 52.0 g. of a mixture of 9α-fluoro-11β,20α-dihydroxy-3-oxo-16α-methyl-1,4-pregnadiene-21-oic acid and 9α-fluoro-11β, 20β-dihydroxy-3-oxo-16α-methyl-1,4-pregnadiene-21-oic acid is obtained as a solid crystal cake.

c. 36.0 g. of the just-described acid mixture is combined with 200 ml. of methanol and cooled to 0° C. An ether solution of diazomethane in 1 liter of ether is added thereto in incremental portions; this ether solution has been obtained from 30 g. of nitrosomethylurea by decomposition with 40% potassium hydroxide solution. The mixture is stored for another hour at room temperature. The solvent is then evacuated after carefully destroying the excess of diazomethane with 5 ml. of glacial acetic acid. The residue is taken up in methylene chloride and the solution is washed repeatedly with wate,r dried over anhydrous sodium sulfate, and the crude product is chromatographed on 750 g. of silica gel. With 6–9% methylene chloride/acetone, the elution product is 2.1 g. of the methyl ester of 9α-fluoro-11β,20α-dihydroxy-3-oxo-16α-methyl-1,4-pregnadiene-21-oic acid. After recrystallization from acetone/hexane, 1.22 g. of pure product is produced, m.p. 199.3° C. $[\alpha]_D^{25} = +2.8°$ (chloroform). With 10–12% methylene chloride/acetone, the elution yields 23.8 g. of a mixture of the 20α- and 20β-compound, and 13–14% methylene chloride/acetone yields as the eluted product 1.19 g. of the methyl ester of 9α-fluoro-11β,20β-dihydroxy-3-oxo-16α-methyl-1,4-pregnadiene-21-oic acid. The crude product is recrystallized from acetone/hexane, thus obtaining 794 mg. of this compound, m.p. 206.5° C. $[\alpha]_D^{25} = +23°$ (chloroform).

d. 18.3 g. of a mixture of the 20α- and 20β-compound is oxidized with active manganese(IV) oxide under the conditions described in Example 1(b). The crude product is chromatographed on silica gel with an acetone/hexane gradient and recrystallized from acetone/hexane, thus producing 8.52 g. of the methyl ester of 9α-fluoro-11β-hydroxy-3,20-dioxo-16α-methyl-1,4-pregnadiene-21-oic acid, m.p. 216–217° C. $[\alpha]_D^{25} = +144°$ (chloroform). UV: $\epsilon_{239} = 16,300$ (methanol).

e. 500 mg. of the methyl ester of 9α-fluoro-11β-hydroxy-3,20-dioxo-16α-methyl-1,4-pregnadiene-21-oic acid is oxidized as described in Example 11(c) and recrystallized from acetone/hexane. Yield: 367 mg. of the methyl ester of 9α-fluoro-3,11,20-trioxo-16α-methyl-1,4-pregnadiene-21-oic acid, m.p. 157.6° C. $[\alpha]_D^{25} = +187°$ (chloroform). UV: $\epsilon_{235} = 16,300$ (methanol).

EXAMPLE 15 a. Under the conditions set forth in Example 2(a), with 7.0 g. of 11 β,21-dihydroxy-16α-methyl-1,4-pregnadiene-3,20-dione, copper(II) acetate and butanol, 5.8 g. of a mixture is obtained consisting of 11 β,20α-dihydroxy-3-oxo-16α-methyl-1,4-pregnadiene-21-oic acid butyl ester and 11 β,20β-dihydroxy-3-oxo-16α-methyl-1,4-pregnadiene-21-oic acid butyl ester, as well as the pure compounds: 230 mg. of the butyl ester of 11 β,20α-dihydroxy-3-oxo-16α-methyl-1,4-pregnadiene-21-oic acid, m.p. 166.3°C. (from methylene chloride/diisopropyl ether). $[\alpha]_D^{25} = +2.7°$ (chloroform). UV: $\epsilon_{244} = 14,800$ (methanol); and 880 mg. of the butyl ester of 11 β,20β-dihydroxy-3-oxo-16α-methyl-1,4-pregnadiene-21-oic acid, m.p. 177.7°C. (from acetone/hexane). $[\alpha]_D^{25} = +12.7°$ (chloroform). UV: $\epsilon_{244} = 14,900$ (methanol).

b. 5.8 g. of the thus-obtained mixture is reacted under the conditions disclosed in Example 3(a) with manganese(IV) oxide. The crude product is chromatographed. With 9–10% acetone/hexane, after recrystallization from acetone/hexane, one obtains 2.88 g. of the butyl ester of 11β-hydroxy-3,20-dioxo-16α-methyl-1,4-pregnadiene-21-oic acid, m.p. 149.8°C. $[\alpha]_D^{25} = +151°$ (chloroform). UV: $\epsilon_{243} = 15,900$ (methanol).

c. 1.0 g. of the butyl ester of 11β-hydroxy-3,20-dioxo-16α-methyl-1,4-pregnadiene-21-oic acid is oxidized as described in Example 3(c), worked up, and recrystallized from methylene chloride/diisopropyl ether, thus producing 583 mg. of the butyl ester of 3,11,20-trioxo-16α-methyl-1,4-pregnadiene-21-oic acid, m.p. 127.9°C $[\alpha]_D^{25} = +208°$ (chloroform). UV: $\epsilon_{239} = 15,900$ (methanol).

EXAMPLE 16 a. 20.0 g. of 6α-fluoro-11 β,21-dihydroxy-16α-methyl-4-pregnene-3,20-dione is reacted under the conditions set forth in Example 2(a), with copper(II) acetate and butanol, thus obtaining 15.3 g. of a mixture of the butyl ester of 6α-fluoro-11 β,20α-dihydroxy-3-oxo-16α-methyl-4-pregnene-21-oic acid and the butyl ester of 6α-fluoro-11 β,20β-dihydroxy-3-oxo-16α-methyl-4-pregnene-21-oic acid and 300 mg. of the butyl ester of 6α-fluoro-11 β,20α-dihydroxy-3-oxo-16β-methyl-4-pregnene-31-oic acid, m.p. 94°C. (from methylene chloride/diisopropyl ether). $[\alpha]_D^{25} = +54°$ (chloroform). UV: $\epsilon_{237} = 15,000$ (methanol), as well as 2.8 g. of the butyl ester of 6α-fluoro-11 β,20β-dihydroxy-3-oxo-16-α-methyl-4-pregnene-21-oic acid, m.p. 139°C. (from acetone/hexane). $[\alpha]_D^{25} = +65°$ (chloroform). UV: $\epsilon_{237} = 14,900$ (methanol).

b. 15.3 g. of the above-produced mixture is reacted with manganese(IV) oxide under the conditions disclosed in Example 3(a). The crude product is chromatographed. With 9–10% acetone/hexane, and after recrystallization from acetone/hexane, one obtains 4.08 g. of the butyl ester of 6α-fluoro-11β-hydroxy-3,20-dioxo-16α-methyl-4-pregnene-21-oic acid, m.p. 188.0°C. $[\alpha]_D^{25} = +176°$ (chloroform). UV: $\epsilon_{236} = 16,100$ (methanol).

c. 1.25 g. of the butyl ester of 6α-fluoro-11β-hydroxy-3,20-dioxo-16α-methyl-4-pregnene-21-oic acid is oxidized with Jones reagent as indicated in Example 3(c) and worked up. The crude product is recrystallized from methylene chloride/diisopropyl ether, thus obtaining 1.08 g. of the butyl ester of 6α-fluoro-3,11,20-trioxo-16α-methyl-4-pregnene-21-oic acid, m.p. 133.4°C. $[\alpha]_D^{25} = +210°$ (chloroform). UV: $\epsilon_{233} = 15,700$ (methanol).

EXAMPLE 17

A solution of 3.0 g. of the butyl ester of 6α-fluoro-3,11,20-trioxo-16α-methyl-1,4-pregnadiene-21-oic acid in 100 ml. of methanol is combined with a solution of 500 mg. of potassium hydroxide in 10 ml. of water and agitated for 15 minutes at room temperature under an argon atmosphere. The reaction mixture is concentrated under vacuum to one-half its volume and poured into 0.5% hydrochloric acid. The thus-precipitated product is filtered off and dissolved in methylene chloride. The solution is washed with water, dried over sodium sulfate, and concentrated under vacuum. The residue is triturated with ether/hexane (2:8) and made to crystallize, thus obtaining 2.21 g. of 6α-fluoro-3,11,20-trioxo-16α-methyl-1,4-pregnadiene-21-oic acid, m.p. 165.9°C. (under decomposition). $[\alpha]_D^{25} = +191°$ (chloroform). UV: $\epsilon_{238} = 15,300$ (methanol).

EXAMPLE 18

A solution of 500 mg. of 6α-fluoro-3,11,20-trioxo-16α-methyl-1,4-pregnadiene-21-oic acid in 100 ml. of methanol is combined with 11.9 ml. of methanolic 0.1N sodium hydroxide solution. The solvent is evaporated under vacuum, and the oily residue is mixed under vigorous agitation with 250 ml. of ether. The thus-produced precipitate is vacuum-filtered and dried under vacuum. Yield: 444 mg. of the sodium salt of 6α-fluoro-3,11,20-trioxo-16α-methyl-1,4-pregnadiene-21-oic acid. $[\alpha]_D^{25} = +187$ (methanol).

EXAMPLE 19 a. Under the conditions described in Example 14(a-d), 25.0 g. of 11β,17α,21-trihydroxy-1,4-pregnadiene-3,20-dione is converted into the methyl ester of 11β-hydroxy-3,20-dioxo-1,4-pregnadiene-21-oic acid, yield: 5.7 g.

5.7 g. of the methyl ester of 11β-hydroxy-3,20-dioxo-1,4-pregnadiene-21-oic acid is transesterified with ethanol under the conditions indicated in Example 3(b), thus obtaining 2.09 g. of the ethyl ester of 11β-hydroxy-3,20-dioxo-1,4-pregnadiene-21-oic acid, m.p. 188°–189°C. $[\alpha]_D^{25} = +175°$ (chloroform). UV: $\epsilon_{243} = 15,700$ (methanol).

b. 1.5 g. of the ethyl ester of 11β-hydroxy-3,20-dioxo-1,4-pregnadiene-21-oic acid is oxidized as described in Example 3(c). The crude product is chromatographed on silica gel and recrystallized from acetone/hexane. Yield: 569 mg. of the ethyl ester of 3,11,20-trioxo-1,4-pregnadiene-21-oic acid, m.p. 139.3°C. $[\alpha]_D^{25} = +237°$ (chloroform). UV: $\epsilon_{238} = 16,000$ (methanol).

EXAMPLE 20

A solution of 450 mg. of the methyl ester of 6α-fluoro-9α-chloro-3,11,20-trioxo-16α-methyl-1,4-pregnadiene-21-oic acid in 50 ml. of butanol is combined with 20 mg. of potassium tert.-butylate and heated under argon for 3 hours to 50°C. The mixture is then diluted with methylene chloride, washed with 1% acetic acid, sodium bicarbonate solution, and water, and the solution is dried over sodium sulfate and concentrated under vacuum. The residue is chromatographed on silica gel. With 15–20% acetone/hexane and after trituration with ether, the product thus obtained is 153 mg. of the butyl ester of 6α-fluoro-9α-chloro-3,11,20-trioxo-16α-methyl-1,4pregnadiene-21-oic acid, m.p. 127.4°C. $[\alpha]_D^{25} = +231°$ (chloroform). UV: $\epsilon_{235} = 16,200$ (methanol).

EXAMPLE 21

250 mg. of the butyl ester of 6α-fluoro-3,11,20-trioxo-16α-methyl-1,4-pregnadiene-21-oic acid is transesterified as described in Example 20 in allyl alcohol. The crude product is chromatographed on silica gel and recrystallized from ether. Yield: 87 mg. of the propenyl ester of 6α-fluoro-3,11,20-trioxo-16α-methyl-1,4-pregnadiene-21-oic acid, m.p. 130.2°C. $[\alpha]_D^{25} = +191°$ (chloroform). UV: $\epsilon_{237} = 16,600$ (methanol).

EXAMPLE 22 a. 1.50 g. of the ethyl ester of 11β-hydroxy-3,20-dioxo-1,4-pregnadiene-21-oic acid is dissolved in 10 ml. of butanol and mixed with 100 mg. of potassium tert.-butylate. After a reaction time of 15 hours at room temperature, the reaction mixture is diluted with methylene chloride and washed with 1% acetic acid, saturated sodium bicarbonate solution, and water. The crude product is chromatographed on silica gel. With 11–14% acetone/hexane, and after recrystallization from acetone/hexane, 717 mg. of the butyl ester of 11β-hydroxy-3,20-dioxo-1,4-pregnadiene-21-oic acid is obtained, m.p. 189°C. $[\alpha]_D^{25} = +135°$ (chloroform). UV: $\epsilon_{241} = 17,000$ (methanol).

b. 400 mg. of the butyl ester of 11β-hydroxy-3,20-dioxo-1,4-pregnadiene-21-oic acid is oxidized as described in Example 3c. The crude product is chromatographed in silica gel and recrystallized from acetone/hexane. Yield: 141 mg. of 3,11,20-trioxo-1,4-pregnadiene-21-oic acid butyl ester, m.p. 99.0° C. $[\alpha]_D^{25} = +229°$ (chloroform). UV: $\epsilon_{238} = 16,000$ (methanol).

EXAMPLE 23 a. 2.0 g. of 6α-fluoro-11α,21-dihydroxy-16α-methyl-1,4-pregnadiene-3,20-dione is dissolved in 250 ml. of methanol and mixed with 500 mg. of copper(II) acetate. The solution is agitated for 45 minutes while passing air therethrough. Then, the mixture is diluted with methylene chloride, washed with 5% ammonium chloride solution and water, dried over sodium sulfate, and the solvent is evaporated under vacuum. Yield: 2.05 g. of 6α-fluoro-11α-hydroxy-3,20-dioxo-16α-methyl-1,4-pregnadien-21-al as the crude product.

b. The thus-obtained product is dissolved in 100 ml. of methanol, the solution is combined with 300 mg. of potassium cyanide, 2.0 ml. of acetic acid, and 5 g. of manganese(IV) oxide and agitated for 30 minutes at room temperature. The manganese(IV) oxide is filtered off, the filtrate is diluted with methylene chloride, washed with water, dried, and evaporated. The residue is chromatographed on silica gel. With 8–12% acetone/hexane, the product is 1.37 g. of the methyl ester of 6α-fluoro-11α-hydroxy-3,20-dioxo-16α-methyl-1,4-pregnadiene-21-oic acid.

c. 500 mg. of this compound is oxidized with Jones reagent as described in Example 3(c). The crude product is recrystallized from acetone/hexane. Yield: 271 mg. of the methyl ester of 6α-fluoro-3,11,20-trioxo-16α-methyl-1,4-pregnadiene-21-oic acid, m.p. 193.3° C. $[\alpha]_D^{25} = +201°$ (chloroform). UV: $\epsilon_{238} = 16,400$ (methanol).

EXAMPLE 24

Ointment Composition:

0.01% Methyl ester of 6α-fluoro-3,11,20-trioxo-16α-methyl-1,4-pregnadiene-21-oic acid
2.50% "Allercur" hexachlorophenate, micronized, particle size about 8 μ ("Allercur" — registered trademark for 1-p-chlorobenzyl-2-pyrrolidylmethylbenzimidazole)

6.00% "Hostaphat" KW 340 (tertiary ester of o-phosphoric acid and wax alcohol tetraglycol ether)
0.10% Sorbic acid
10.00% Neutral oil ("Migloyol 812")
3.50% Stearyl alcohol
1.50% Lanolin, anhydrous, DAB 6 [German Pharmacopoeia]
76.39% Desalted water

EXAMPLE 25

Ointment Composition:

0.01 g. Methyl ester of 6α-fluoro-3,11,20-trioxo-16α-methyl-1,4-pregnadiene-21-oic acid
5.00 g. White wax, DAB 6
5.00 g. Lanolin, anhydrous, DAB 6
20.00 g. Vaseline, white, DAB 6
25.00 g. Amphocerin K "Dehydag"
14.97 g. Paraffin oil, liquid, DAB 6
30.00 g. Water, desalted
0.02 g. Crematest perfume oil No. 6580 "Dragee"

EXAMPLE 26

Eyedrop Composition (Oily):

100 mg. of the methyl ester of 6α-fluoro-9α-chloro-3,11,20-trioxo-16α-methyl-1,4-pregnadiene-21-oic acid is dissolved in
100 ml. of castor oil.

After adding 200 mg. of chloramphenicol (or another bacteriostatic agent), the solution is aseptically filtered and bottled under sterilization.

EXAMPLE 27

Composition of Eardrops:

100 mg. of the methyl ester of 6α-fluoro-3,11,20-trioxo-16α-methyl-1,4-pregnadiene-21-oic acid is dissolved in 1,2-propyleneglycol/ethyl alcohol (9:1). The solution is brought to a volume of 100 ml. and then 200 mg. of chloramphenicol is added thereto.

EXAMPLE 28 a. 9.5 g. of 11β,21-dihydroxy-16α-methyl-4-pregnene-3,20-dione is reacted under the conditions described in Example 1(a). The crude product is chromatographed on silica gel, thus obtaining 5.32 g. of a mixture of the butyl esters of 11β,20α-dihydroxy- and 11β,20β-dihydroxy-3-oxo-16α-methyl-4-pregnene-21-oic acid and 58 mg. of the butyl ester of 11β,20α-dihydroxy-3-oxo-16α-methyl-4-pregnene-21-oic acid, m.p. 110° C. (from acetone/hexane); $[\alpha]_D^{25} = +60°$ (chloroform); UV: $\epsilon_{242} = 15,800$ (methanol); and 1.40 g. of the butyl ester of 11β,20β-dihydroxy-3-oxo-16α-methyl-4-pregnene-21-oic acid, m.p. 139° C. (from methylene chloride/diisopropyl ether); $[\alpha]_D^{25} = +77°$ (chloroform); UV: $\epsilon_{242} = 15,700$ (methanol).

b. 5.32 g. of the mixture of epimers is reacted with manganese(IV) oxide under the conditions set forth in Example 1(b). The crude product is chromatographed. With 10–13% acetone/hexane and after recrystallization from acetone/hexane, the yield is 1.62 g. of the butyl ester of 11β-hydroxy-3,20-dioxo-16α-methyl-4-pregnene-21-oic acid, m.p. 162° C. $[\alpha]_D^{25} = +198°$ (chloroform).

c. 1.0 g. of the butyl ester of 11β-hydroxy-3,20-dioxo-16α-methyl-4-pregnene-21-oic acid is oxidized in 40 ml. of acetone at 0° C. with 1 ml. of Jones reagent. After a reaction time of 30 minutes, the mixture is stirred into 500 ml. of saturated sodium chloride solution. The thus-precipitated product is isolated and recrystallized from acetone/hexane, thus obtaining 689 mg. of the butyl ester of 3,11,20-trioxo-16α-methyl-4-pregnene-21-oic acid, m.p. 150.8° C. $[\alpha]_D^{25} = +230°$ (chloroform). UV: $\epsilon_{238} = 16,500$ (methanol).

EXAMPLE 29 a. 6.0 g. of 6α-fluoro-11β,21-dihydroxy-16α-methyl-1,4-pregnadiene-3,20-dione is combined with 180 ml. of n-butanol and 1.6 g. of copper(II) acetate and allowed to stand for 8 days at room temperature. Then, the mixture is filtered, the filtrate is concentrated, the residue is mixed with 10% ammonium hydroxide solution and extracted with methylene chloride. The extract is washed, dried, and concentrated under vacuum. The thus-obtained crude product is combined with 30 ml. of methylene chloride and 30 g. of active manganese(IV) oxide ("precipitate for synthesis purposes" by Merck A.G.) and heated to the boiling point for 6 hours under reflux. Thereafter, the manganese(IV) oxide is filtered off, the filtrate concentrated, and the residue is recrystallized from hexane/acetone, thus obtaining 1.08 g. of the butyl ester of 6α-fluoro-11β-hydroxy-3,20-dioxo-16α-methyl-1,4-pregnadiene-21-oic acid.

b. A solution of 2.0 g. of the butyl ester of 6α-fluoro-11β-hydroxy-3,20-dioxo-16α-methyl-1,4-pregnadiene-21-oic acid in 30 ml. of pyridine and 5 ml. of acetic anhydride is combined with 100 mg. of 4-dimethylaminopyridine and allowed to stand overnight at room temperature. The reaction product is precipitated with ice water, filtered off, and taken up in methylene chloride. The solution is washed repeatedly with water, dried, and evaporated. The residue is chromatographed on silica gel. With 17–21% acetone/hexane and after recrystallization from acetone/hexane, the yield is 1.80 g. of the butyl ester of 6α-fluoro-11β-acetoxy-3,20-dioxo-16α-methyl-1,4-pregnadiene-21-oic acid, m.p. 148.3° C. $[\alpha]_D^{25} = +160°$ (chloroform). UV: $\epsilon_{239} = 17,400$ (methanol).

EXAMPLE 30

750 mg. of the butyl ester of 6α-fluoro-11β-acetoxy-3,20-dioxo-16α-methyl-1,4-pregnadiene-21-oic acid is dissolved in 20 ml. of methanol. The solution is mixed with 50 mg. of potassium tert.-butylate and maintained at room temperature for 8 hours. The mixture is then diluted with methylene chloride, acidified with 1% acetic acid, washed several times with water, dried over sodium sulfate, and concentrated under vacuum. The residue is chromatographed on silica gel. Elution with 45–50% acetone/hexane yields 207 mg. of the methyl ester of 6α-fluoro-11β-acetoxy-3,20-dioxo-16α-methyl-1,4-pregnadiene-21-oic acid (recrystallized from acetone/hexane), m.p. 226.8° C. $[\alpha]_D^{25} = +164°$ (chloroform). UV: $\epsilon_{239} = 17,300$ (methanol).

EXAMPLE 31

2.0 g. of the butyl ester of 6α-fluoro-11β-hydroxy-3,20-dioxo-16α-methyl-1,4-pregnadiene-21-oic acid is esterified analogously to Example 29(b) in pyridine with butyric acid anhydride in the presence of 4-dimethylaminopyridine. The crude product is chromatographed on silica gel. With 14–17% acetone/hexane, and after recrystallization from hexane/diisopropyl ether, the yield is 1.50 g. of the butyl ester of 6α-fluoro-11β-butyryloxy-3,20-dioxo-16α-methyl-1,4-pregnadiene-21-oic acid, m.p. 93.1° C. $[\alpha]_D^{25} = +151°$ (chloroform). UV: $\epsilon_{239} = 17,400$ (methanol).

EXAMPLE 32

750 mg. of the butyl ester of 6α-fluoro-11β-butyryloxy-3,20-dioxo-16α-methyl-1,4-pregnadiene-21oic acid is converted into the methyl ester as described in Example 30. The crude product is chromatographed on silica gel. With 17–21% acetone/hexane, and after recrystallization from acetone/hexane, one obtains 313 mg. of the methyl ester of 6α-fluoro-11β-butyryloxy-3,20-dioxo-16α-methyl-1,4-pregnadiene-21-oic acid, m.p. 103.7° C. $[\alpha]_D^{25} = +156°$ (chloroform). UV: $\epsilon_{239} = 17,400$ (methanol).

EXAMPLE 33 a. One gram of 9α-fluoro-11β,21-dihydroxy-16α-methyl-1,4-pregnadiene-3,20-dione is dissolved in 125 ml. of methanol and combined with a solution of 250 mg. of copper(II) acetate in 125 ml. of methanol. The mixture is stirred for 15 minutes at room temperature while passing air therethrough, and then is combined with methylene chloride, washed with 5% ammonium chloride solution and water, and concentrated under vacuum. The thus-obtained product is dissolved in 50 ml. of methanol. The solution is mixed with 165 mg. of potassium cyanide, 1.0 ml. of acetic acid, and 5 g. of manganese(IV) oxide and agitated for 30 minutes at room temperature. Then the mixture is filtered, the filtrate diluted with methylene chloride, washed with water, dried, and concentrated under vacuum. The residue is chromatographed over a silica gel column, recrystallized from acetone/hexane, and the methyl ester of 9α-fluoro-11β-hydroxy-3,20-dioxo-16α-methyl-1,4-pregnadiene-21-oic acid is thus produced, m.p. 215° C.

b. One gram of the methyl ester of 9α-fluoro-11β-hydroxy-3,20-dioxo-16α-methyl-1,4-pregnadiene-21-oic acid is esterified analogously to Example 29(b) in pyridine with butyric acid anhydride in the presence of 4-dimethylaminopyridine. The crude product is chromatographed on silica gel. With 37–45% acetone/hexane, and after recrystallization from ether/hexane, 815 mg. of the methyl ester of 9α-fluoro-11β-butyryloxy-3,20-dioxo-16α-methyl-1,4-pregnadiene-21-oic acid is obtained, m.p. 83.6° C. $[\alpha]_D^{25} = +158°$ (chloroform). UV: $\epsilon_{236} = 16,400$ (methanol).

EXAMPLE 34

Under the conditions of Example 33(a), 5.0 g. of 6α-fluoro-21-hydroxy-11β-acetoxy-16α-methyl-4-pregnene-3,20-dione is converted into the methyl ester of 6α-fluoro-11β-acetoxy-3,20-dioxo-16α-methyl-4-pregnene-21-oic acid.

One gram of the thus-obtained crude product is mixed with 1.5 g. of 2,3-dichloro-5,6-dicyanobenzoquinone and 50 ml. of absolute benzene, and the mixture is refluxed for 24 hours. Then, the reaction mixture is allowed to cool, filtered, and concentrated under vacuum to dryness. The residue is purified by way of a silica gel column, thus obtaining 106 mg. of the methyl ester of 6α-fluoro-11β-acetoxy-3,20-dioxo-16α-methyl-1,4-pregnadiene-21-oic acid, m.p. 225.4° C.

EXAMPLE 35

Ointment Composition:

0.01% Methyl ester of 6α-fluoro-11β-acetoxy-3,20-dioxo-16α-methyl-1,4-pregnadiene-21-oic acid
2.50% "Allercur" hexachlorophenate, micronized, particle size about 8 μ ("Allercur" = registered trademark for 1-p-chlorobenzyl-2-pyrrolidylmethylbenzimidazole)
6.00% "Hostaphat KW 340" (tertiary ester of o-phosphoric acid and wax alcohol tetraglycol ether)
0.10% Sorbic acid
10.00% Neutral oil ("Migloyol 812")
3.50% Stearyl alcohol
1.50% Lanolin, anhydrous, DAB 6
76.39% Desalted water

EXAMPLE 36

Ointment Composition:

0.01 g. Butyl ester of 6α-fluoro-11β-acetoxy-3,20-dioxo-16α-methyl-1,4-pregnadiene-21-oic acid
5.00 g. White wax, DAB 6
5.00 g. Lanolin, anhydrous, DAB 6
20.00 g. Vaseline, white, DAB 6
25.00 g. Amphocerin K "Dehydag"
14.97 g. Paraffin oil, liquid, DAB 6
30.00 g. Water, desalted
0.02 g. Crematest perfume oil No. 6580 "Dragee"

EXAMPLE 37

Eyedrop Composition (Oily):

100 mg. of the butyl ester of 6α-fluoro-11β-acetoxy-3,20-dioxo-16α-methyl-1,4-pregnadiene-21-oic acid is dissolved in
100 ml. of castor oil.

The solution is filtered under sterile conditions after adding 200 mg. of chloramphenicol (or another bacteriostatic agent) and bottled aseptically.

EXAMPLE 38 a. 26.0 g. of 6α-fluoro-21-hydroxy-16α-methyl-4-pregnene-3,20-dione is dissolved in 1000 ml. of butanol and combined with 13 g. of copper(II) acetate in 1000 ml. of butanol. The solution is agitated for 10 days at room temperature, filtered, and concentrated under vacuum. The crude product is chromatographed on silica gel. With 10–12% acetone/hexane, and after recrystallization from methylene chloride/diisopropyl ether, 459 mg. of the butyl ester of 6α-fluoro-20α-hydroxy-3-oxo-16α-methyl-4-pregnene-21-oic acid is produced, m.p. 115.1° C. $[\alpha]_D^{25} = +32°$ (chloroform). UV: $\epsilon_{236} = 15,700$ (methanol).

With 12–13% acetone/hexane, the elution product is 22.0 g. of a mixture of the butyl esters of 6α-fluoro-20α- and 6α-fluoro-20β-hydroxy-3-oxo-16α-methyl-4-pregnene-21-oic acid.

With 13–15% acetone/hexane, and after recrystallization from methylene chloride/diisopropyl ether, the thus-obtained product is 751 mg. of the butyl ester of 6α-fluoro-20β-hydroxy-3-oxo-16α-methyl-4-pregnene-21-oic acid, m.p. 128.8° C. $[\alpha]_D^{25} = +51°$ (chloroform). UV: $\epsilon_{231} = 16,000$ (methanol).

b. 22.0 g. of the thus-obtained mixture of epimers is dissolved in 550 ml. of acetone and mixed at 0° C. with 26.5 ml. of Jones reagent. After 40 minutes, the mixture is precipitated with water; the precipitate is isolated and recrystallized from acetone/hexane. Yield: 16.5 g. of the butyl ester of 6α-fluoro-3,20-dioxo-16α-methyl-4-pregnene-21-oic acid, m.p. 115.5° C. $[\alpha]_D^{25} = + 159°$ (chloroform). UV: $\epsilon_{234} = 16,600$ (methanol).

EXAMPLE 39

A solution of 1.0 g. of the butyl ester of 6α-fluoro-3,20-dioxo-16α-methyl-4-pregnene-21-oic acid in 20 ml. of methanol is combined with 100 mg. of potassium tert.-butylate and allowed to react for 16 hours under nitrogen at room temperature. The reaction mixture is diluted with methylene chloride, washed neutral with water, dried, and concentrated. The residue is recrystallized from acetone/hexane. Yield: 325 mg. of the methyl ester of 6α-fluoro-3,20-dioxo-16α-methyl-4-pregnene-21-oic acid, m.p. 133.9° C. $[\alpha]_D^{25} = + 165°$ (chloroform). UV: $\epsilon_{235} = 16,800$ (methanol).

EXAMPLE 40

A solution of 1.0 g. of the butyl ester of 6α-fluoro-3,20-dioxo-16α-methyl-4-pregnene-21-oic acid in 10 ml. of methanol is combined with 2 ml. of 2N sodium hydroxide solution and agitated for 20 minutes under nitrogen. After dilution with 100 ml. of water, the mixture is washed with methylene chloride and the aqueous phase is acidified with hydrochloric acid. The precipitated product is isolated and recrystallized from ethyl acetate at −30° C. Yield: 453 mg. of 6α-fluoro-3,20-dioxo-16α-methyl-4-pregnene-21-oic acid, m.p. 205.1° C. (decomposition).
$[\alpha]_D^{25} = + 165°$ (chloroform).
UV: $\epsilon_{236} = 14,700$ (methanol).

EXAMPLE 41 a. 30.0 g. of 21-hydroxy-16α-methyl-4-pregnene-3,20-dione is reacted, as described in Example 38(a), with copper(II) acetate in the presence of butanol. The crude product is chromatographed on silica gel. With 10–11% acetone/hexane, and after recrystallization from acetone/hexane, one obtains 1.21 g. of the butyl ester of 20α-hydroxy-3-oxo-16α-methyl-4-pregnene-21-oic acid, m.p. 89.1° C. $[\alpha]_D^{25} = + 32°$ (chloroform). UV: $\epsilon_{241} = 16,500$ (methanol).

With 11–14% acetone, 22.0 g. of a mixture of the butyl esters of 20α- and 20β-hydroxy-3-oxo-16α-methyl-4-pregnene-21-oic acid is obtained.

With 14–16% acetone/hexane, and after recrystallization from acetone/hexane, the yield is 685 mg. of the butyl ester of 20β-hydroxy-3-oxo-16α-methyl-4-pregnene-21-oic acid, m.p. 53.4° C. $[\alpha]_D^{25} = + 51°$ (chloroform). UV: $\epsilon_{241} = 15,500$ (methanol).

b. 22.0 g. of the thus-produced mixture of epimers is oxidized in 550 ml. of acetone with 26.5 of Jones reagent. The crude product is chromatographed.

With 11–14% acetone/hexane, and after recrystallization from acetone/hexane, 10.0 g. of the butyl ester of 3,20-dioxo-16α-methyl-4-pregnene-21-oic acid is produced, m.p. 76.2° C. $[\alpha]_D^{25} = + 173°$ (chloroform). UV: $\epsilon_{241} = 17,500$ (methanol).

EXAMPLE 42

1.0 g. of the butyl ester of 3,20-dioxo-16α-methyl-4-pregnene-21-oic acid is converted into the methyl ester under the conditions indicated in Example 39. Yield: 435 mg. of the methyl ester of 3,20-dioxo-16α-methyl-4-pregnene-21-oic acid, m.p. 118.0° C. $[\alpha]_D^{25} = + 183°$ (chloroform). UV: $\epsilon_{240} = 17,500$ (methanol).

EXAMPLE 43

500 mg. of the butyl ester of 3,20-dioxo-16α-methyl-4-pregnene-21-oic acid is saponified under the conditions described in Example 40. The crude product is recrystallized from ethyl acetate at a low temperature. Yield: 336 mg. of 3,20-dioxo-16α-methyl-4-pregnene-21-oic acid, m.p. 215.7° C. (under decomposition). $[\alpha]_D^{25} = + 183°$ (chloroform). UV: $\epsilon_{240} = 16,500$ (methanol).

EXAMPLE 44

A solution of 1.0 g. of the butyl ester of 6α-fluoro-3,20-dioxo-16α-methyl-4-pregnene-21-oic acid in 30 ml. of benzene is combined with 1.0 g. of 2,3-dichloro-5,6-dicyanobenzoquinone and heated to the boiling point for 24 hours. The solution is then filtered and concentrated under vacuum. The residue is chromatographed with an acetone/hexane gradient on silica gel. After recrystallization from acetone/hexane, 465 mg. of the butyl ester of 6α-fluoro-3,20-dioxo-16α-methyl-1,4-pregnadiene-21-oic acid is obtained as a viscous oil. $[\alpha]_D^{25} = + 108°$ (chloroform). UV: $\epsilon_{241} = 17,900$ (methanol).

EXAMPLE 45

750 mg. of the butyl ester of 16α-methyl-3,20-dioxo-4-pregnene-21-oic acid is dehydrogenated under the conditions set forth in Example 44. The crude product is chromatographed and recrystallized from acetone/hexane, thus obtaining 256 mg. of the butyl ester of 3,20-dioxo-16α-methyl-1,4-pregnadiene-21-oic acid.

EXAMPLE 46 a. 1.0 g. of 21-hydroxy-4-pregnene-3,20-dione is dissolved in 125 ml. of methanol and combined with a solution of 250 mg. of copper(II) acetate in 125 ml. of methanol. For 30 minutes, air is passed through the solution, and the latter is then combined with a solution of 500 mg. of ethylenediaminetetraacetic acid in 50 ml. of water, adjusted to pH 9 with 1N sodium hydroxide solution. The mixture is concentrated under vacuum at 40° C. and extracted with ethyl acetate. The extract is dried over sodium sulfate and evaporated under vacuum. As the residue, 1.1 g. of 3,20-dioxo-4-pregnen-21-al is obtained as a viscous oil.

b. The thus-obtained product is dissolved in 50 ml. of methanol, the solution is combined with 1.0 g. of potassium cyanide, 1 ml. of acetic acid, and 10 g. of manganese(IV) oxide and agitated for 5 minutes at room temperature. The manganese(IV) oxide is filtered off, the filtrate is diluted with methylene chloride, washed with water, dried, and evaporated. The crude product is chromatographed on silica gel. With 9–12% acetone/hexane, and after recrystallization from acetone/hexane, 545 mg. of the methyl ester of 3,20-dioxo-4-pregnene-21-oic acid is obtained, m.p. 141.9° C. $[\alpha]_D^{25} = + 208°$ (chloroform). UV: $\epsilon_{240} = 16,700$ (methanol).

c. Under the conditions described in Example 44, 350 mg. of the methyl ester of 3,20-dioxo-4-pregnene-21-oic acid is dehydrogenated. After chromatography and recrystallization from acetone/hexane, 119 mg. of the methyl ester of 3,20-dioxo-1,4-pregnadiene-21-oic acid is produced, m.p. 142.2°C. $[\alpha]_D^{25} = + 156°$ (chloroform).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A pregnanoic acid derivative of the formula

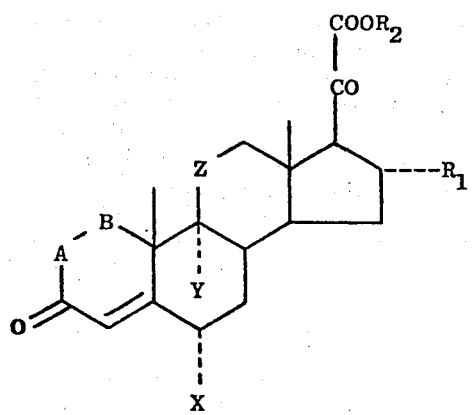

wherein X is a hydrogen atom, a halogen atom, or methyl, Y is a hydrogen atom or a halogen atom, Z is carbonyl, or when Y is a hydrogen atom, methylene, $R_1$ is a hydrogen atom or methyl, $R_2$ is a hydrogen atom, an alkali metal atom, or saturated or unsaturated hydrocarbon of 1–12 carbon atoms which is unsubstituted or substituted by up to 3 of hydroxy, halo, alkoxy, carboxy, carbalkoxy, amino, alkylamino, dialkylamino, nitro, sulfato and alkali metal salts thereof wherein each alkyl group is of 1 to 4 carbon atoms, —A—B— is —CH=CH— or —CCl=CH— or when at least one of X, Y and $R_1$ is other than hydrogen, —CH$_2$—CH$_2$—.

2. A compound of claim 1 wherein Z is carbonyl.
3. A compound of claim 1 wherein $R_2$ is a hydrogen atom.
4. A compound of claim 3 wherein $R_2$ is an alkali metal.
5. A compound of claim 1 wherein $R_1$ is methyl.
6. A compound of claim 1, butyl ester of 6α-fluoro-3,11,20-trioxo-16α-methyl-1,4-pregnadiene-21-oic acid.
7. A compound of claim 1, methyl ester of 6α-fluoro-3,11,20-trioxo-16α-methyl-1,4-pregnadiene-21-oic acid.
8. A compound of claim 1, ethyl ester of 6α-fluoro-3,11,20-trioxo-16α-methyl-1,4-pregnadiene-21-oic acid.
9. A compound of claim 1, propyl ester of 6α-fluoro-3,11,20-trioxo-16α-methyl-1,4-pregnadiene-21-oic acid.
10. A compound of claim 1, isopropyl ester of 6α-fluoro-3,11,20-trioxo-16α-methyl-1,4-pregnadiene-21-oic acid.
11. A compound of claim 1, tert.-butyl ester of 6α-fluoro-3,11,20-trioxo-16α-methyl-1,4-pregnadiene-21-oic acid.
12. A compound of claim 1, (1,1-dimethylpropyl) ester of 6α-fluoro-3,11,20-trioxo-16α-methyl-1,4-pregnadiene-21-oic acid.
13. A compound of claim 1, (3-methylbutyl) ester of 6α-fluoro-3,11,20-trioxo-16α-methyl-1,4-pregnadiene-21-oic acid.
14. A compound of claim 1, cyclohexyl ester of 6α-fluoro-3,11,20-trioxo-16α-methyl-1,4-pregnadiene-21-oic acid.
15. A compound of claim 1, methyl ester of 6α-fluoro-2-chloro-3,11,20-trioxo-16α-methyl-1,4-pregnadiene-21-oic acid.
16. A compound of claim 1, methyl ester of 6α-fluoro-9α-chloro-3,11,20-trioxo-16α-methyl-1,4-pregnadiene-21-oic acid.
17. A compound of claim 1, methyl ester of 6α,9α-difluoro-3,11,20-trioxo-16α-methyl-1,4-pregnadiene-21-oic acid.
18. A compound of claim 1, butyl ester of 6α,9α-difluoro-3,11,20-trioxo-16α-methyl-1,4-pregnadiene-21-oic acid.
19. A compound of claim 1, methyl ester of 9α-fluoro-3,11,20-trioxo-16α-methyl-1,4-pregnadiene-21-oic acid.
20. A compound of claim 1, butyl ester of 3,11,20-trioxo-16α-methyl-1,4-pregnadiene-21-oic acid.
21. A compound of claim 1, butyl ester of 6α-fluoro-3,11,20-trioxo-16α-methyl-4-pregnene-21-oic acid.
22. A compound of claim 1, 6α-fluoro-3,11,20-trioxo-16α-methyl-1,4-pregnadiene-21-oic acid.
23. A compound of claim 1, sodium salt of 6α-fluoro-3,11,20-trioxo-16α-methyl-1,4-pregnadiene-21-oic acid.
24. A compound of claim 1, ethyl ester of 3,11,20-trioxo-1,4-pregnadiene-21-oic acid.
25. A compound of claim 1, butyl ester of 6α-fluoro-9α-chloro-3,11,20-trioxo-16α-methyl-1,4-pregnadiene-21-oic acid.
26. A compound of claim 1, propenyl ester of 6α-fluoro-3,11,20-trioxo-16α-methyl-1,4-pregnadiene-21-oic acid.
27. A compound of claim 1, butyl ester of 3,11,20-trioxo-1,4-pregnadiene-21-oic acid.
28. A compound of claim 1, butyl ester of 3,11,20-trioxo-16α-methyl-4-pregnene-21-oic acid.
29. A compound of claim 1, butyl ester of 6α-fluoro-3,20-dioxo-16α-methyl-1,4-pregnadiene-21-oic acid.
30. A compound of claim 1, butyl ester of 3,20-dioxo-16α-methyl-1,4-pregnadiene-21-oic acid.
31. A compound of claim 1, methyl ester of 3,20-dioxo-1,4-pregnadiene-21-oic acid.
32. A compound of claim 1, butyl ester of 6α-fluoro-3,20-dioxo-16α-methyl-4-pregnene-21-oic acid.
33. A compound of claim 1, methyl ester of 6α-fluoro-3,20-dioxo-16α-methyl-4-pregnene-21-oic acid.
34. A compound of claim 1, 6α-fluoro-3,20-dioxo-16α-methyl-4-pregnene-21-oic acid.
35. A compound of claim 1, butyl ester of 3,20-dioxo-16α-methyl-4-pregnene-21-oic acid.
36. A compound of claim 1, methyl ester of 3,20-dioxo-16α-methyl-4-pregnene-21-oic acid.
37. A compound of claim 1, 3,20-dioxo-16α-methyl-4-pregnene-21-oic acid.

* * * * *